(12) United States Patent
Flickinger et al.

(10) Patent No.: US 9,795,494 B2
(45) Date of Patent: Oct. 24, 2017

(54) SPINAL IMPLANT ALIGNMENT GUIDE SYSTEMS

(71) Applicant: MediTech Spine, LLC, Atlanta, GA (US)

(72) Inventors: Eric Flickinger, Atlanta, GA (US); Adam Sclafani, Uniontown, OH (US); Jason Gromek, Cleveland, OH (US); Sangwook Tim Yoon, Decatur, GA (US)

(73) Assignee: MEDITECH SPINE, LLC, Atlanta, GA (US)

( * ) Notice: Subject to any disclaimer, the term of this patent is extended or adjusted under 35 U.S.C. 154(b) by 768 days.

(21) Appl. No.: 14/095,636

(22) Filed: Dec. 3, 2013

(65) Prior Publication Data

US 2014/0156008 A1 Jun. 5, 2014

Related U.S. Application Data

(60) Provisional application No. 61/732,487, filed on Dec. 3, 2012.

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC .......... *A61F 2/4611* (2013.01); *A61F 2/4465* (2013.01); *A61F 2002/2835* (2013.01); *A61F 2002/30383* (2013.01); *A61F 2002/30617* (2013.01); *A61F 2002/30784* (2013.01); *A61F 2002/30904* (2013.01); *A61F 2002/4629* (2013.01)

(58) Field of Classification Search
CPC .......... A61F 2/44; A61F 2/442; A61F 2/4455; A61F 2/446; A61F 2/4465; A61F 2/447; A61F 2/46; A61F 2/4603; A61F 2/4611; A61F 2002/443; A61F 2002/444; A61F 2002/4475; A61F 2002/4622; A61F 2002/4625; A61F 2002/4628; A61F 2002/4629; A61F 2002/4635; A61B 17/88; A61B 17/8872; A61B 17/8841; A61B 2017/0256

See application file for complete search history.

(56) References Cited

U.S. PATENT DOCUMENTS

| | | | |
|---|---|---|---|
| 7,575,580 B2 * | 8/2009 | Lim | A61F 2/4465 606/246 |
| 8,043,293 B2 * | 10/2011 | Warnick | A61F 2/4465 606/249 |
| 2012/0277869 A1 * | 11/2012 | Siccardi | A61F 2/4465 623/17.16 |

* cited by examiner

*Primary Examiner* — Kevin T Truong
*Assistant Examiner* — Tracy Kamikawa
(74) *Attorney, Agent, or Firm* — Kilpatrick Townsend & Stockton LLP

(57) ABSTRACT

Systems for improved methods of performing a spinal fusion procedure that include an implant having an alignment guide system. The alignment guide system may include one or more guide lines configured to provide a visual indication when the implant is properly aligned within the disc space. In some embodiments, the system includes one or more tamp levelers that also aid with the proper alignment of the implant within the disc space.

19 Claims, 20 Drawing Sheets

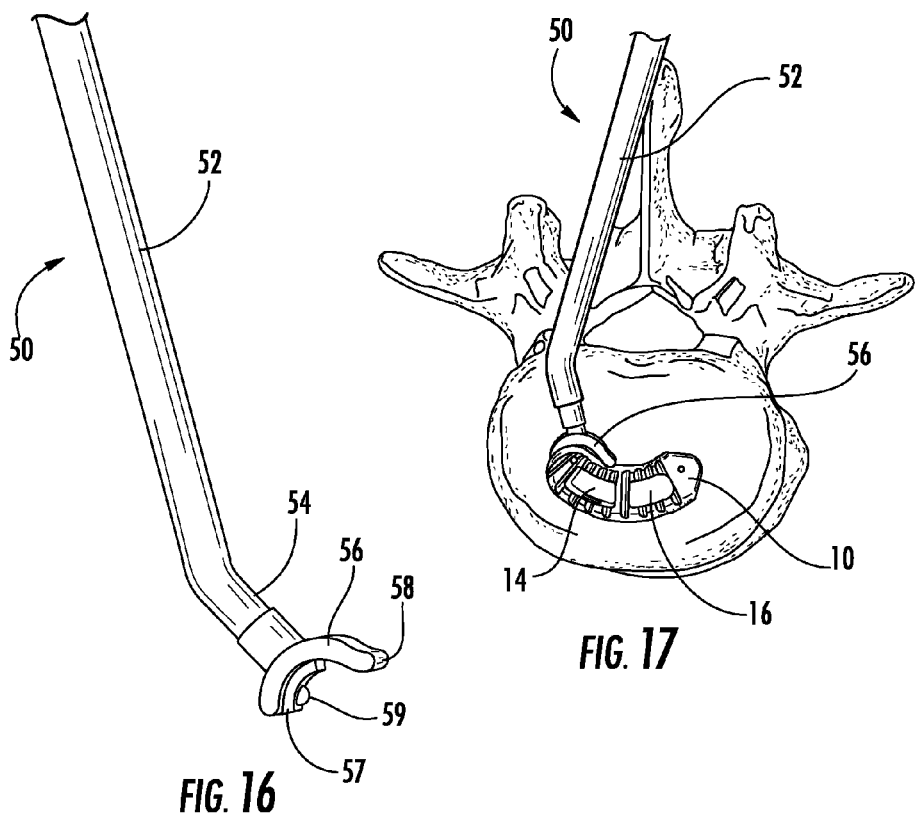

SPINAL IMPLANT ALIGNMENT GUIDE SYSTEMS

RELATED APPLICATION

This application claims the benefit of U.S. Provisional Application No. 61/732,487 filed Dec. 3, 2012 and titled "Implant With Alignment Guides and Tamp Levelers," the entire contents of which are hereby incorporated by reference.

FIELD OF THE INVENTION

This invention relates generally to spinal surgery and, in particular, to alignment systems for positioning a spinal implant.

BACKGROUND

The spinal column is a flexible column formed from a linear series of vertebral bones separated by intervertebral discs. These discs reduce friction between adjacent vertebrae and absorb compression forces applied to the spinal column. A vertebra includes an anterior body and a posterior arch that surrounds the spinal cord. Spinal nerves extend from each side of the spinal cord and exit the column at the vertebral foramen, which is formed by the posterior arch. Articular processes, including the superior articular process and the inferior articular process, are small flat projections on the surfaces of the arches.

There are four facet joints associated with each vertebra, and these joints interlock with adjacent vertebrae. In this manner, facets on opposing processes determine the range and direction of movement between adjacent vertebrae, hence the flexibility of the spinal column. The facet joints maintain spinal stability, protect the disc from excessive stress, and assist the discs in allowing motion and controlling shear forces. These joints are vulnerable to degenerative spinal disorders.

Degenerative disc disease is typically caused by a loss of disc space height, leading to a narrowing of the neural foramen and subsequent neural compression, and causing back and radicular pain. Instability of the posterior elements can lead to a condition known as spondylolisthesis, in which a vertebral body slips forward in relation to an adjacent vertebrae. This movement of the vertebral body narrows the foramen and results in painful pressure on the nerve roots.

Degenerative disc disease often may be resolved through a spinal fusion procedure during which an interbody implant is implanted between the bodies of two adjacent vertebrae. Such interbody implants may be formed from titanium, carbon fiber, allograft, or other suitable material including, but not limited to, biocompatible materials such as PEEK™, available from Invibio®. Implantation of a substitute implant is designed to reestablish normal disc height, provide immediate stability to the motion segment, and provide a matrix for fusion. When the implant grows into the existing bone, the fusion becomes solid and movement is eliminated at that level. A fusion procedure may also involve the surgical implantation of hardware, such as plates, screws or cages.

Posterior Lumbar Interbody Fusion (PLIF) and Anterior Lumbar Interbody Fusion (ALIF) are two surgical fusion techniques used to treat degenerative disc disease. Transforaminal Lumbar Interbody Fusion (TLIF) is another means of accessing the interbody space. TLIF involves the removal of one facet joint, usually on the more diseased or symptomatic side of the spine. Approaching the disc space and spinal canal from one side of the intervertebral space allows the surgeon to operate with minimal stretching of nerve roots.

In a typical procedure, the patient is positioned using a frame or spine table according to standard procedures, and the surgeon selects an appropriate approach angle based on patient pathology. After an incision is made, the correct level and facet joint are exposed visually and with x-ray verification. A facetectomy is performed and portions of the articular processes are removed as required, and neural elements are protected and/or retracted as necessary. After the disc is removed from the disc space, appropriate distraction is performed.

Depending on the patient's disc space, distraction can be performed with trials or with a paddle distractor. Distraction using modular trials is accomplished by threading individual trials onto the insertion instrument and placing them into the disc space sequentially until the desired disc height is achieved. Distraction using a paddle distractor is achieved by placing the distractor into the disc space and rotating 90 degrees.

Various kidney-shaped (or banana-shaped) implants have been designed to be impacted across the disc space to achieve arthrodesis. Although longer, straight implants have been placed across the disc space with some success, the lordotic angle of the spine is harder to properly match with these straight implants. The kidney-shaped implant helps maintain proper lordosis when it is placed in the anterior third of the disc space.

Proper alignment of the implant is imperative because improper positioning can lead to reduced fusion site stability, as well as improper balance of the spinal column. In some current procedures, proper positioning of a kidney-shaped implant in the disc space requires multiple x-ray images during insertion and placement. Such repeated x-ray imaging is disruptive and costly. Thus, a need exists for a system allowing visualization of proper alignment during the insertion and positioning process.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Disclosed in this patent are implants with alignment guides that allow for visualization of proper alignment during insertion and positioning of an implant in the disc space. Also disclosed are improved instruments for helping position the implant within the disc space.

BRIEF DESCRIPTION OF THE DRAWINGS

FIG. 16 is a perspective view of a tamp according to one embodiment of this invention.

FIG. 17 is a perspective view of a cross section of a portion of the human spine, illustrating use of the tamp of FIG. 16 in positioning an implant.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Implants with Alignment Guides

Embodiments of this invention include an implant having an alignment guide to visually assist the surgeon during implantation of the device. The alignment guide provides an easy reference for the surgeon or other personnel in determining when the implant has been properly aligned within the disc space. In some embodiments, such a guide is particularly useful during posterior surgeries, where the surgeon's view of the disc space into which the implant is implanted is limited and the surgeon must rotate the implant before it is aligned properly.

FIGS. 1-15 illustrate one embodiment a spinal implant 10 that is configured to be implanted between the bodies of two adjacent vertebrae. In some embodiments, as shown in FIGS. 3-6, an end 13 of the implant 10 includes an arcuate surface 11 with a recessed channel 12. Channel 12 is shaped and configured to accommodate a tamp leveler, which is used to guide the implant 10 into position. Examples of various tamp levelers that may be used to help position implant 10 are discussed below and shown in FIGS. 16-33, although any suitable tamp leveler or other instrument may be used to help position implant 10.

Figure 1:
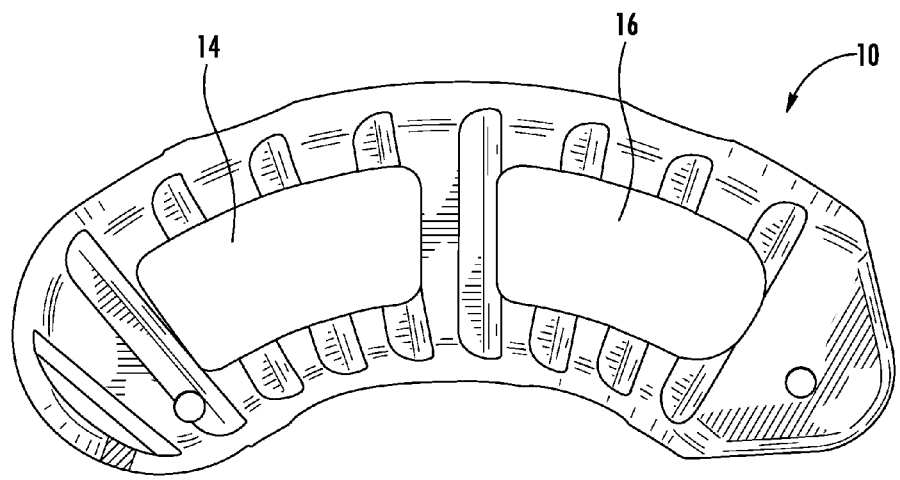
FIG. 1 is a top view of an implant according to one embodiment of this invention.
Figure 2:
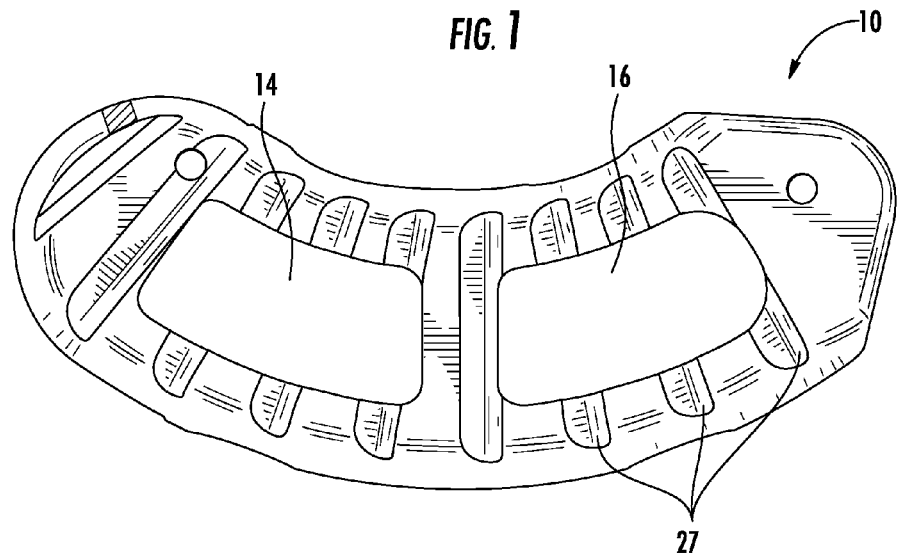
FIG. 2 is a bottom view of the implant of FIG. 1.
Figure 3:
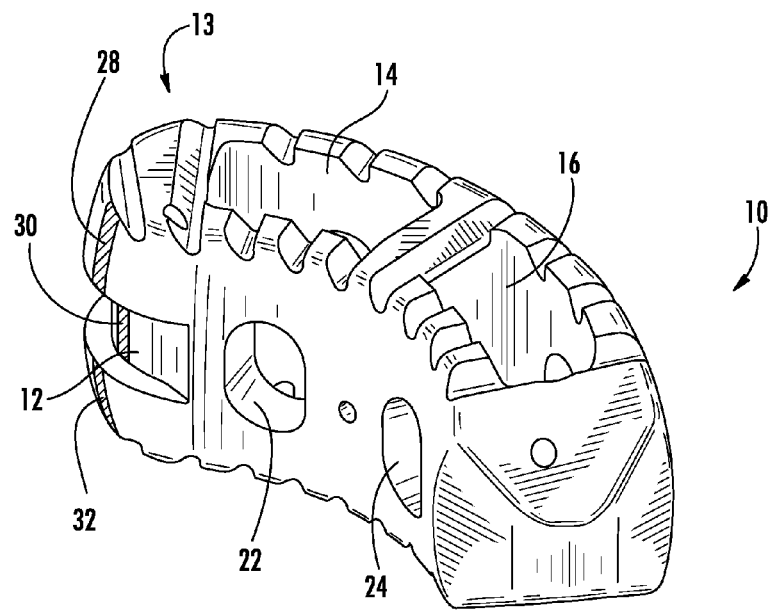
FIG. 3 is a top perspective view of the implant of FIG. 1.
Figure 4:
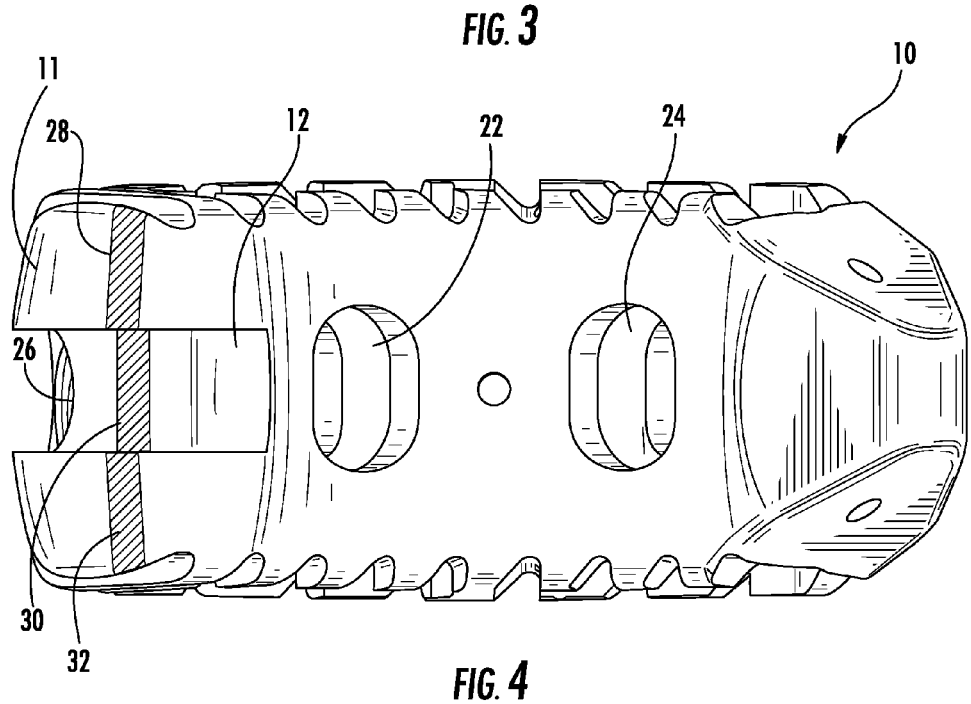
FIG. 4 is a front view of the implant of FIG. 1.
Figure 5:
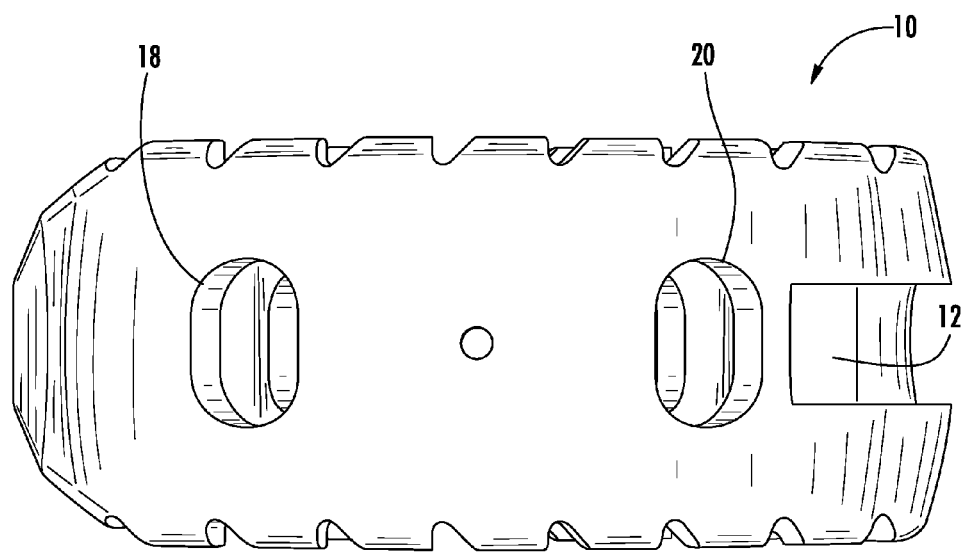
FIG. 5 is a rear view of the implant of FIG. 1.

As shown in FIGS. 1-15, implant 10 may be generally kidney-shaped. Implant 10 may include a plurality of teeth 27 for engaging with the bone. As illustrated, one or more cavities, such as cavities 14, 16, may extend from the top to the bottom of the implant. If desired, suitable bone graft material may be inserted into the cavities 14, 16 to help promote bone growth and fusion of the implant into existing bone. Implant 10 may also include one or more windows, such as first window 18 and second window 20 on the rear of the implant 10 as shown in FIG. 5 and third window 22 and fourth window 24 on the front of the implant as shown in FIGS. 3-4. Windows 18, 20, 22, and 24 may be used to promote fusion of the implant to existing bone and help create bridging bone between the implant, disc space, and the endplates of the vertebral bodies.

Figure 6:
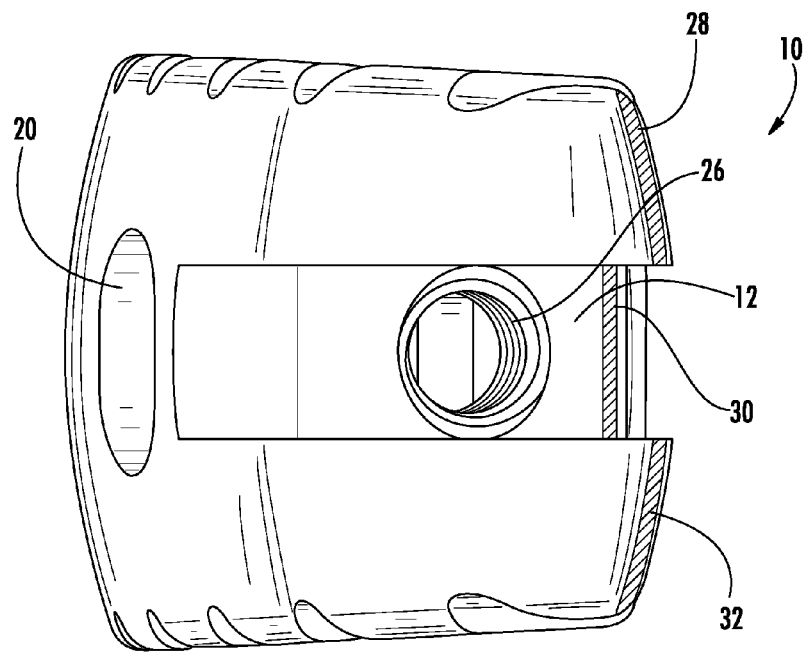
FIG. 6 is an end view of the implant of FIG. 1.

In some embodiments, recessed channel 12 includes an aperture 26 as shown in FIG. 6. Aperture 26 may include a plurality of threads for threading onto an inserter or other instrument used to insert the implant 10 into the disc space. As mentioned, implant 10 also includes at least one alignment guide. In the embodiment illustrated, the alignment guide includes three guide lines 28, 30, and 32 as shown in FIG. 4, although dots, dashes, or any other suitable marking may be used instead of lines. Guide lines 28 and 32 may be positioned along the arcuate surface 11 of the implant, while guide line 30 may be positioned along channel 12. In this way, guide line 30 is recessed with respect to guide lines 28 and 32.

Figure 15:
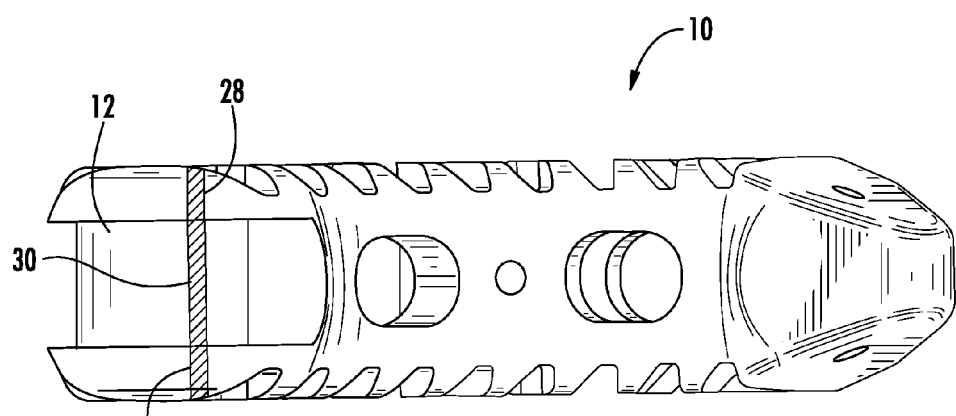
FIG. 15 is a side view of the implant of FIG. 13, indicating proper alignment and positioning of the implant.

Guide lines 28, 30, and 32 are positioned on arcuate surface 11 and channel 12 such that guide line 30 will be in alignment with guide lines 28 and 32 when the implant 10 is oriented as desired (see, e.g., FIG. 15). Specifically, when the implant 10 is properly aligned within the disc space, the three guide lines 28, 30, and 32 substantially align along a single axis to indicate to the surgeon or other personnel that the implant 10 has been rotated to a proper position within the disc space. The three guide lines 28, 30, and 32 are configured such that when the implant 10 is not oriented as desired, the three guide lines 28, 30, and 32 do not align along a single axis (see, e.g., FIGS. 9 and 12).

In some embodiments, the three guide lines 28, 30, and 32 are configured to provide a visual indication based on a 15 degree off vertical line of sight. In other words, the three guide lines 28, 30, and 32 provide the proper visual indication when the surgeon or other personnel is looking at the implant from approximately 15 degrees from vertical. Because the incision is typically so small for the implant, surgeons or other personnel typically will be looking from this same (or similar) 15 degree of vertical line of sight. In some embodiments, the configuration of the guide lines and/or the number of guide lines is adjusted if a different degree of sight is intended.

Figure 7:
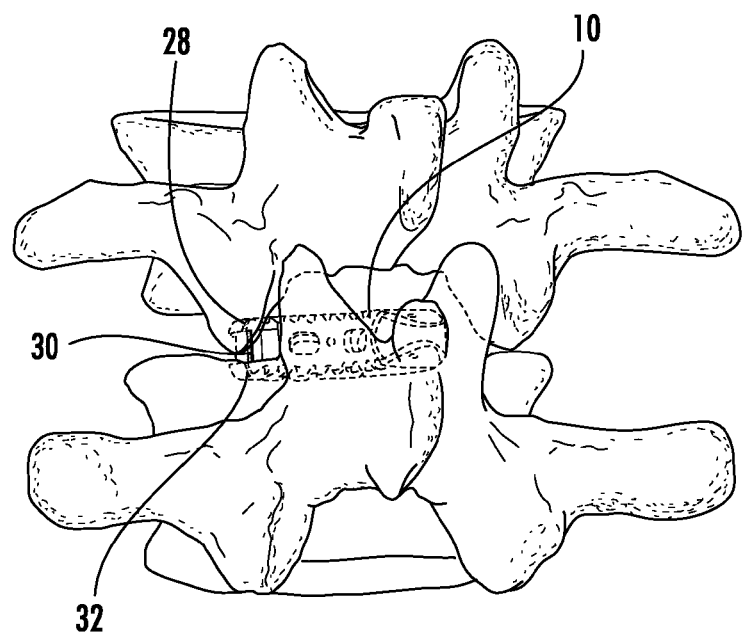
FIG. 7 is a perspective view of an illustration of a portion of the human spine together with the implant of FIG. 1, indicating over rotation of the implant.
Figure 8:
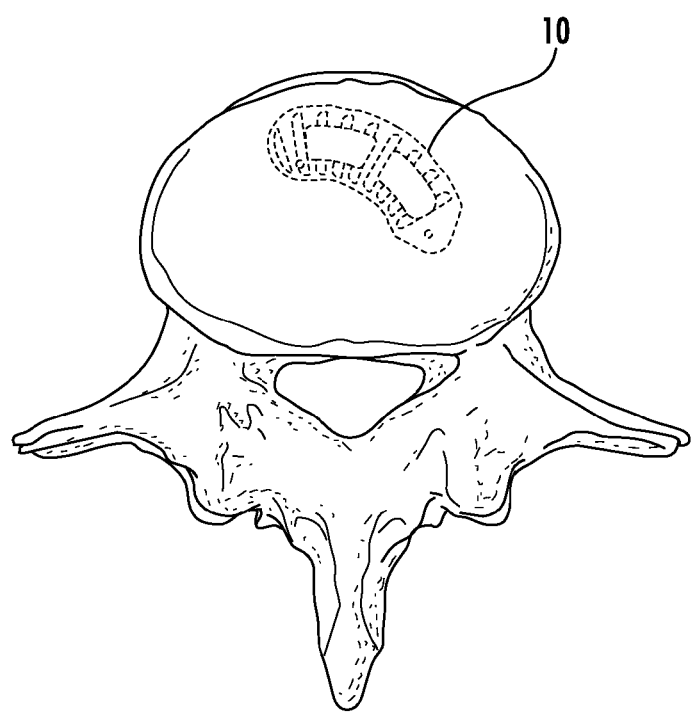
FIG. 8 is another view of the implant and spine of FIG. 7 indicating over rotation of the implant.
Figure 9:
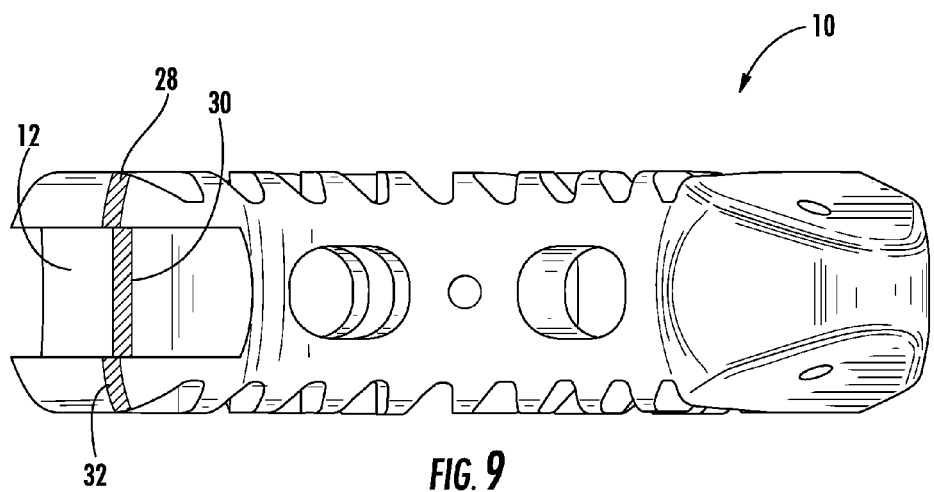
FIG. 9 is a side view of the implant of FIG. 7, indicating over rotation of the implant.

As illustrated in FIGS. 7-15, when viewed from approximately 15 degrees from vertical, the three guide lines will be substantially aligned with one another along a single axis when the implant has been properly aligned in the disc space, and will be misaligned when the implant is not properly aligned. FIGS. 7-9 illustrate the misalignment of three guide lines 28, 30, and 32 when the implant 10 has been over-rotated in the disc space. FIG. 7 is an illustration of the surgeon or other personnel's view into the disc space from approximately 15 degrees of vertical during surgery when the implant is over-rotated. FIG. 8 is a top view of the surgical configuration of the implant with respect to one vertebra after the over-rotation shown in FIG. 7. FIG. 9 shows a side view of the implant 10 in isolation when the guide lines 28, 30, and 32 indicate the implant has been over-rotated as shown in FIGS. 7 and 8.

Figure 10:
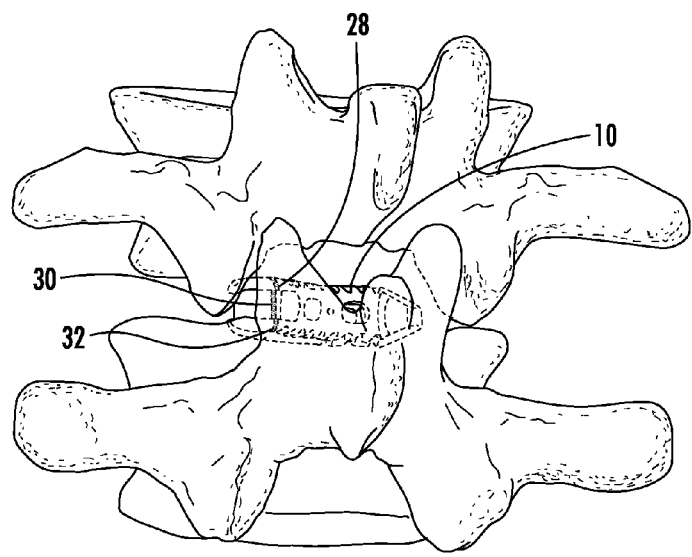
FIG. 10 is a perspective view of an illustration of a portion of the human spine together with the implant of FIG. 1, indicating under rotation of the implant.
Figure 11:
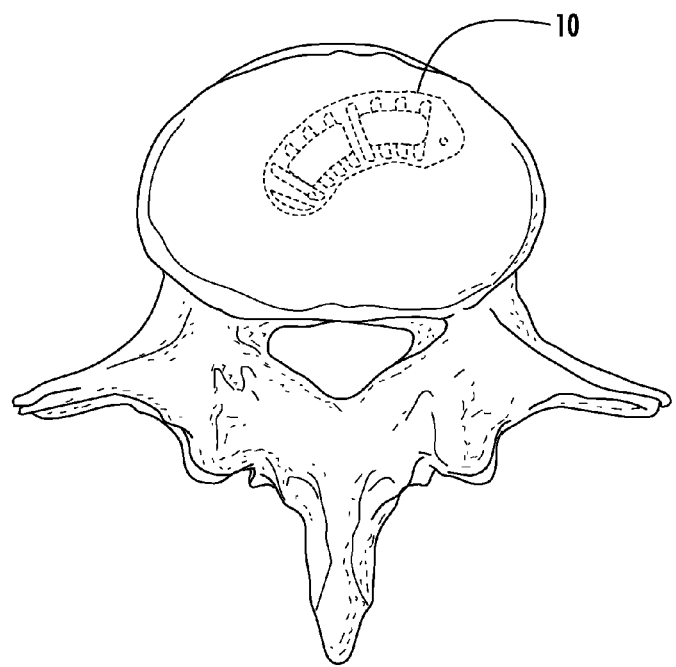
FIG. 11 is another view of the implant and spine of FIG. 10, indicating under rotation of the implant.
Figure 12:
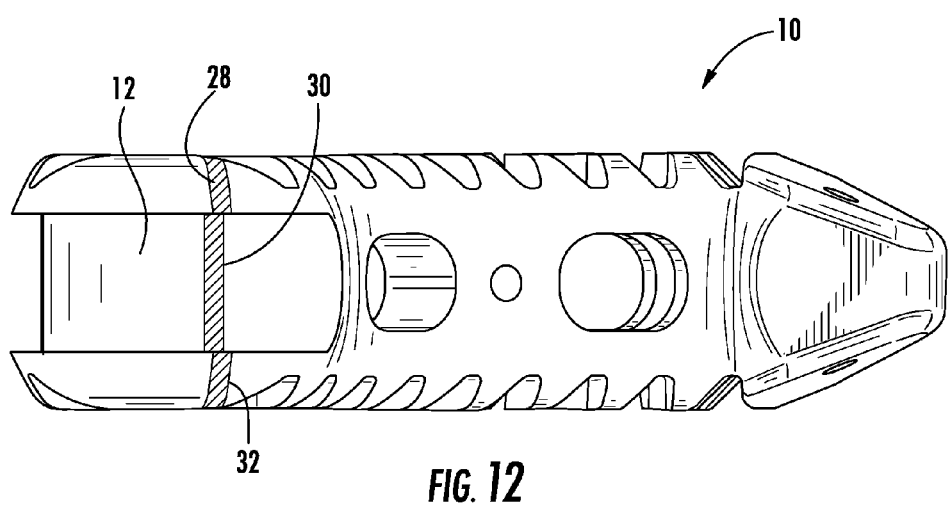
FIG. 12 is a side view of the implant of FIG. 10, indicating under rotation of the implant.

FIG. 10 is an illustration of the surgeon or other personnel's view into the disc space from approximately 15 degrees of vertical during surgery when the implant 10 is under-rotated. FIG. 11 shows a top view of the surgical configuration of the implant 10 with respect to one vertebra after the under-rotation shown in FIG. 10. FIG. 12 shows a side view of the implant 10 in isolation when the guide lines 28, 30, and 32 are misaligned and indicate the implant 10 has been under-rotated as shown in FIGS. 10-11.

Figure 13:
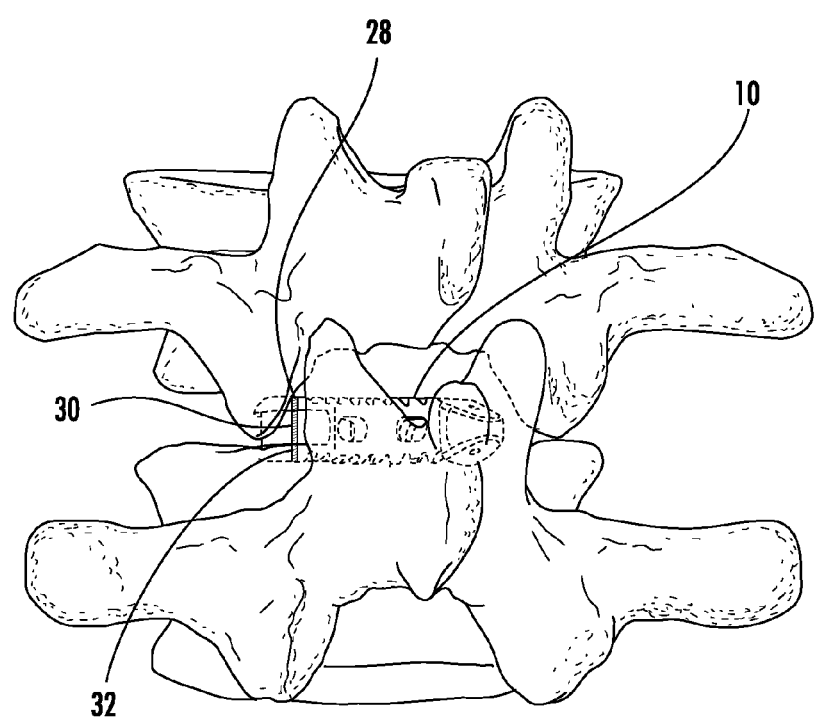
FIG. 13 is a perspective view of an illustration of a portion of the human spine together with the implant of FIG. 1, indicating proper positioning of the implant.
Figure 14:
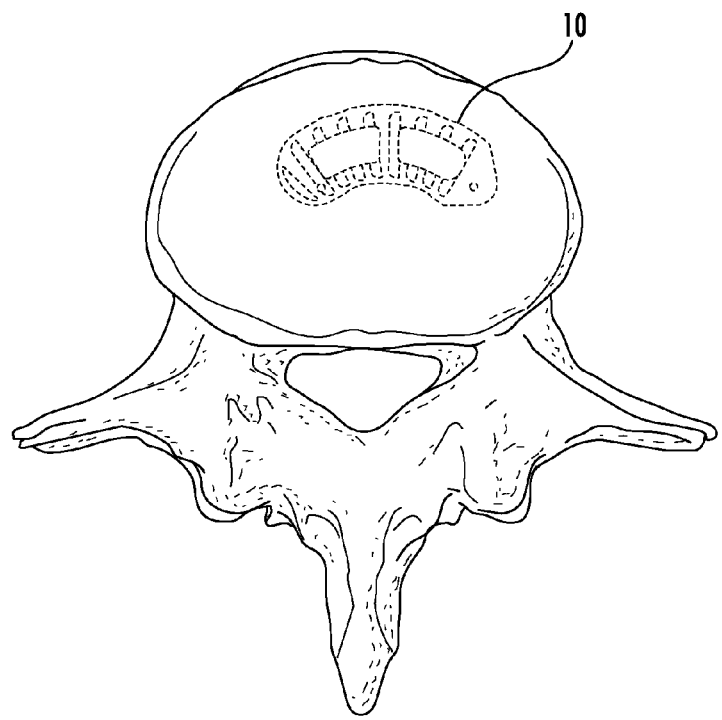
FIG. 14 is another view of the implant and spine of FIG. 13, indicating proper positioning of the implant.

FIG. 13 is an illustration of the surgeon or other personnel's view into the disc space from approximately 15 degrees of vertical during surgery when the implant 10 is properly rotated. FIG. 14 illustrates the surgical configuration of the implant 10 with respect to one vertebra in proper alignment as shown in FIG. 13. FIG. 15 shows a side view of the implant 10 in isolation when the guide lines 28, 30, and 32 substantially align to form a single axis and indicate the implant 10 is in proper alignment.

In this manner, the three guide lines 28, 30, 32 are configured along the implant 10 to serve as an alignment guide system to help indicate proper positioning of the implant in the disc space. As mentioned, variations in the number and configuration of the guide lines is envisioned.

Instruments to Help Position an Implant within the Disc Space

As generally set forth above, during a spinal fusion procedure, the disc space is prepared, the disc is removed from the disc space, and the disc space is distracted and otherwise prepared for the spinal implant. The spinal implant, such as, but not limited to, implant 10 described above, is threaded onto an inserter. The implant is then inserted into the disc space using the inserter and one or more tamp levelers are used to rotate the implant along the disc space into proper position. In some cases, the implant is impacted across the disc space with its convex anterior wall resting up against the anterior annulus.

As shown in FIGS. 16-33 and further described below, one or more tamp levelers or other suitable instrument may be used to help position the implant (such as, but not limited to, implant 10) into the anterior part of the disc space. As noted above, implant 10 includes a channel 12. The tamp levelers disclosed herein are configured to fit together with channel 12 of implant 10 to assist with proper alignment of the implant into the disc space. Although the tamp levelers discussed below are described in connection with implant 10, the tamp levelers disclosed herein can be used with any suitable implant and are not limited to use with implant 10.

FIGS. 16-17 illustrate a tamp leveler 50 according to an embodiment of the invention. Tamp leveler 50 includes a handle (not shown) and a shaft 52 that extends from the handle at any suitable angle. Shaft 52 may include one or more bends if desired to accommodate the patient's anatomy and provide a more unobstructed view into the disc space. In some embodiments, a neck 54 connects an engagement head 56 to the shaft 54, while in other embodiments, engagement head extends directly from the shaft. If used, neck 54 may extend from shaft 52 at any suitable angle and may include any suitable radius of curvature to accommodate the patient's anatomy and the disc space. Engagement head 56 includes a ledge 57 that is shaped and configured to be received within channel 12 of implant 10. Protrusion 59 extends from ledge 58 and is configured to be received within aperture 26 of channel 12. Protrusion 59 may have any suitable cross section and may have any suitable length. In other embodiments, ledge 58 does not include a protrusion. In some embodiments, an end 58 of engagement head 56 is shaped and configured to rest within window 22 of the implant 10, as shown in FIG. 17.

Figures 18, 19:
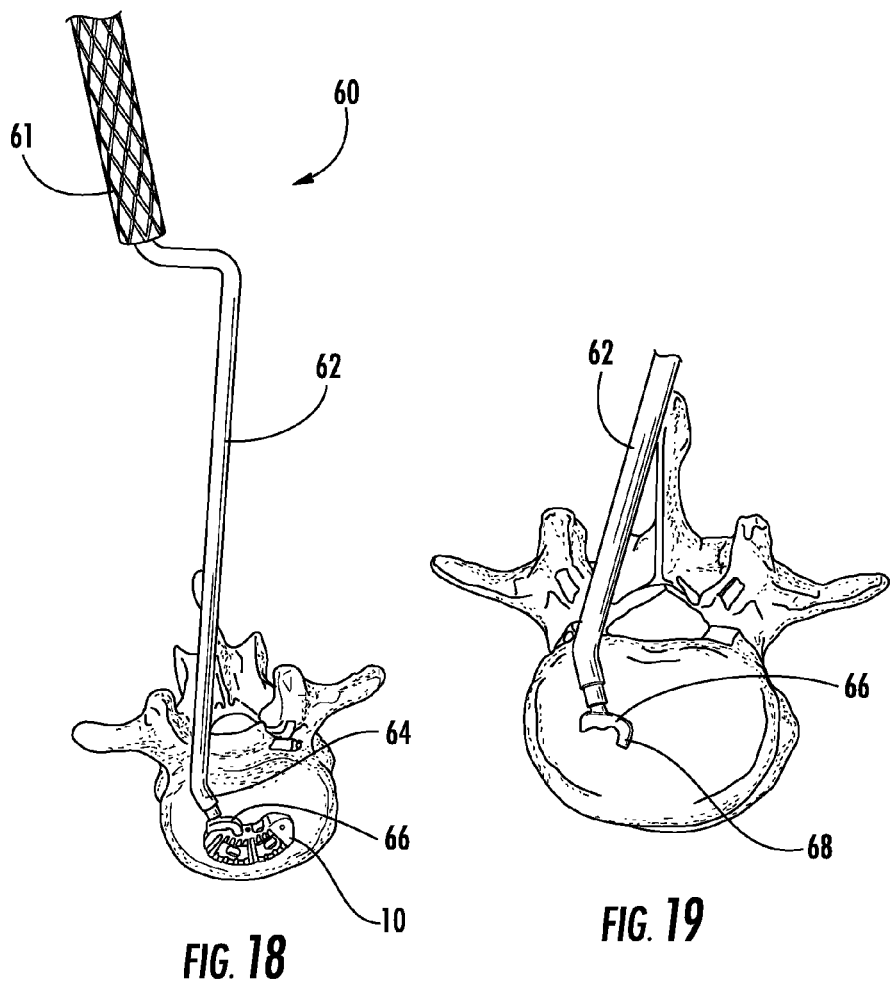
FIG. 18 is a perspective view of a cross section of a portion of the human spine, illustrating use of an another tamp of this invention in positioning an implant.
FIG. 19 is a perspective view of a cross section of a portion of the human spine, illustrating insertion of the tamp of FIG. 18.
Figure 20:
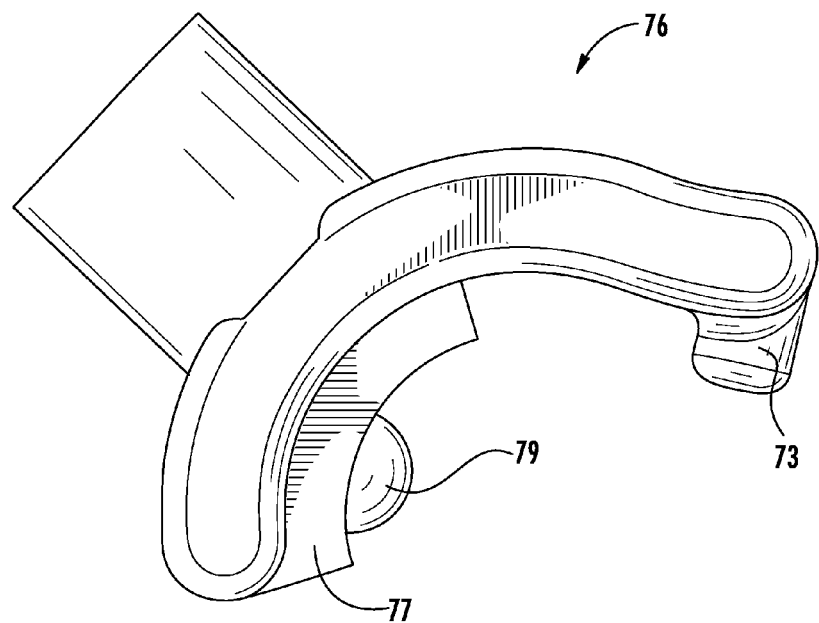
FIG. 20 is a perspective view of another tamp of this invention.

Tamp leveler 60 shown in FIGS. 18-19 includes a handle 61 and a shaft 62 that extends from the handle 61 at any suitable angle. Shaft 62 may include one or more bends if desired to accommodate the patient's anatomy and provide a more unobstructed view into the disc space. In some embodiments, a neck 64 connects an engagement head 66 to the shaft 64. If used, neck 64 may extend from shaft 64 at any suitable angle and may include any suitable radius of curvature to accommodate the patient's anatomy and the disc space. As shown in FIG. 18, an end 68 of engagement head 66 is shaped and configured to hook into window 22 of the implant 10, as shown in FIG. 19.

Figure 21:
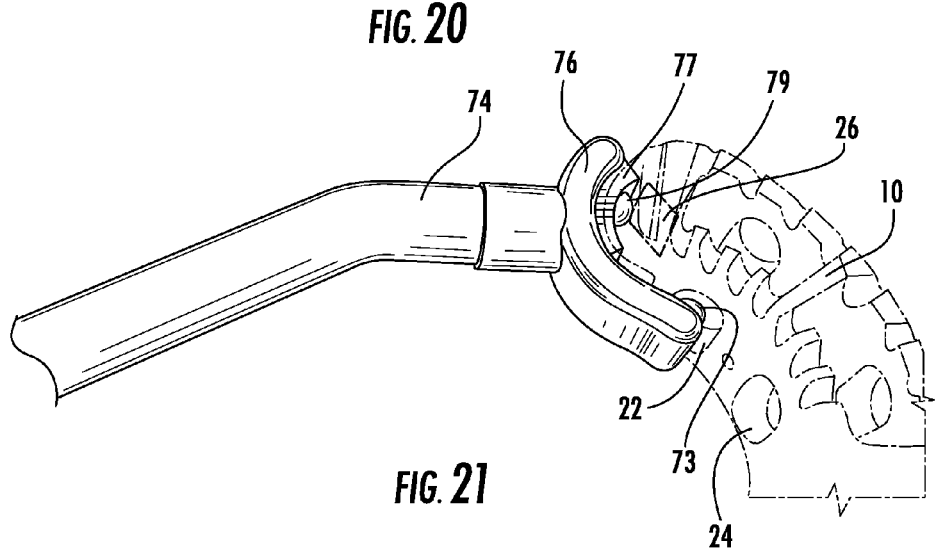
FIG. 21 is a perspective view of the tamp of FIG. 19, coupled to an implant.

Like tamp levelers 50 and 60, tamp leveler 70 shown in FIG. 21 includes an engagement head 76 that extends from a neck 74 at any suitable angle. Like engagement head 56, engagement head 76 includes a ledge 77 that is shaped and configured to be received within channel 12 of implant 10. Protrusion 79 extends from ledge 78 and is configured to be received within aperture 26 of channel 12. In some embodiments, an end 78 of engagement head 56 includes a protrusion 73 that is shaped and configured to hook into window 22 of the implant 10, as shown in FIG. 21. Protrusions 79 and 73 may have any suitable cross section and may have any suitable length.

Figure 22:
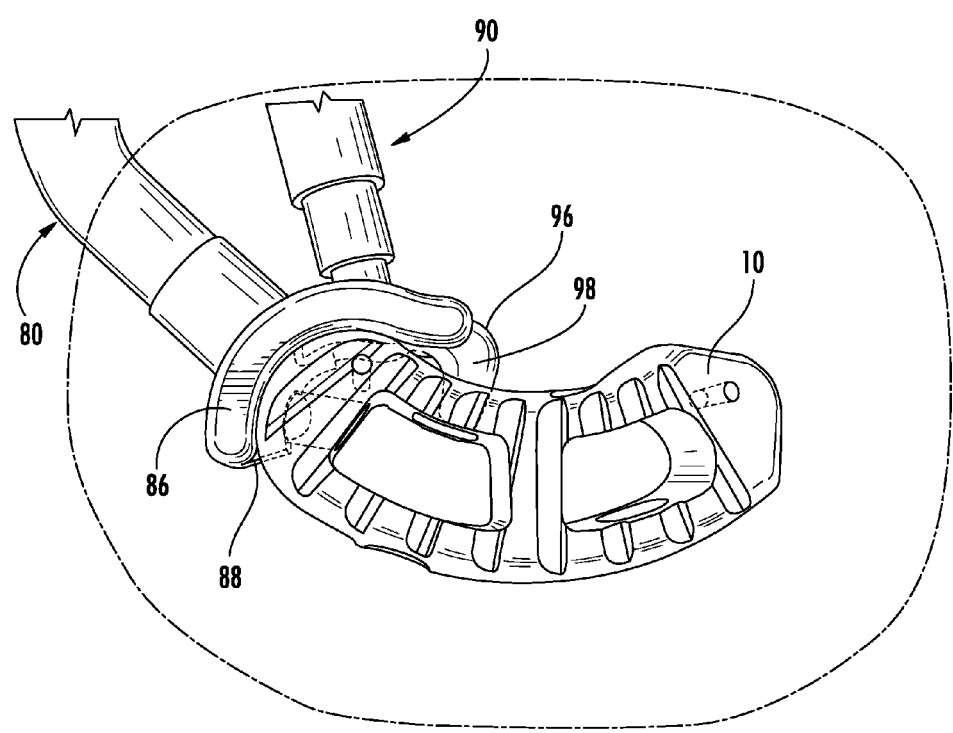
FIG. 22 is an overlay of two tamps of this invention attached to an implant.

FIG. 22 illustrates two tamp levelers 80 and 90 engaged with implant 10 in the disc space. Tamp leveler 80 is configured for more of a lateral or transforaminal approach to the disc space, while tamp leveler 90 is configured for more a direct posterior approach such as PLIF to the disc space, as shown. Tamp leveler 80 includes an engagement head 86 having a ledge 87 configured to be received within the channel 12 of implant 10. Tamp leveler 90 includes an engagement head 96 having an end 98 that is shaped and configured to hook into window 22 of the implant 10, as shown in FIG. 22.

Figure 23:
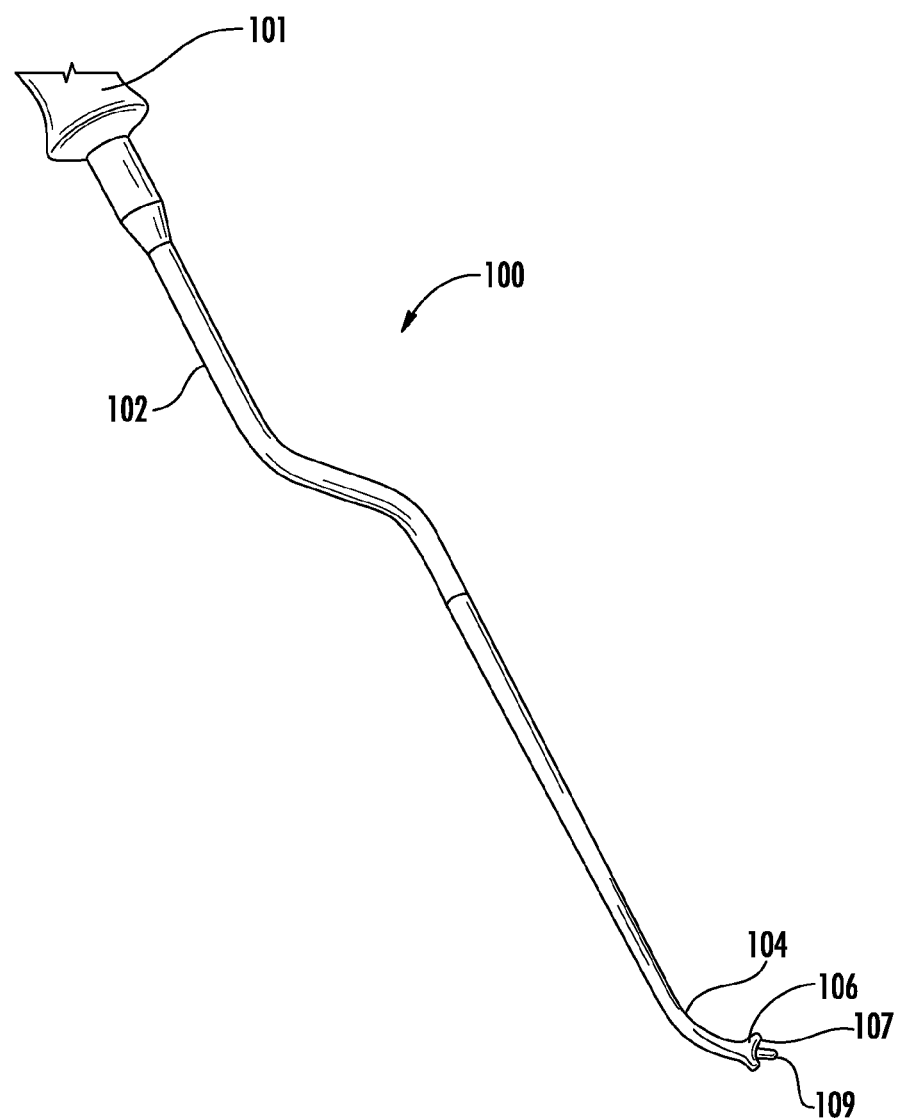
FIG. 23 is a perspective view of another tamp of an embodiment of this invention.
Figure 24:
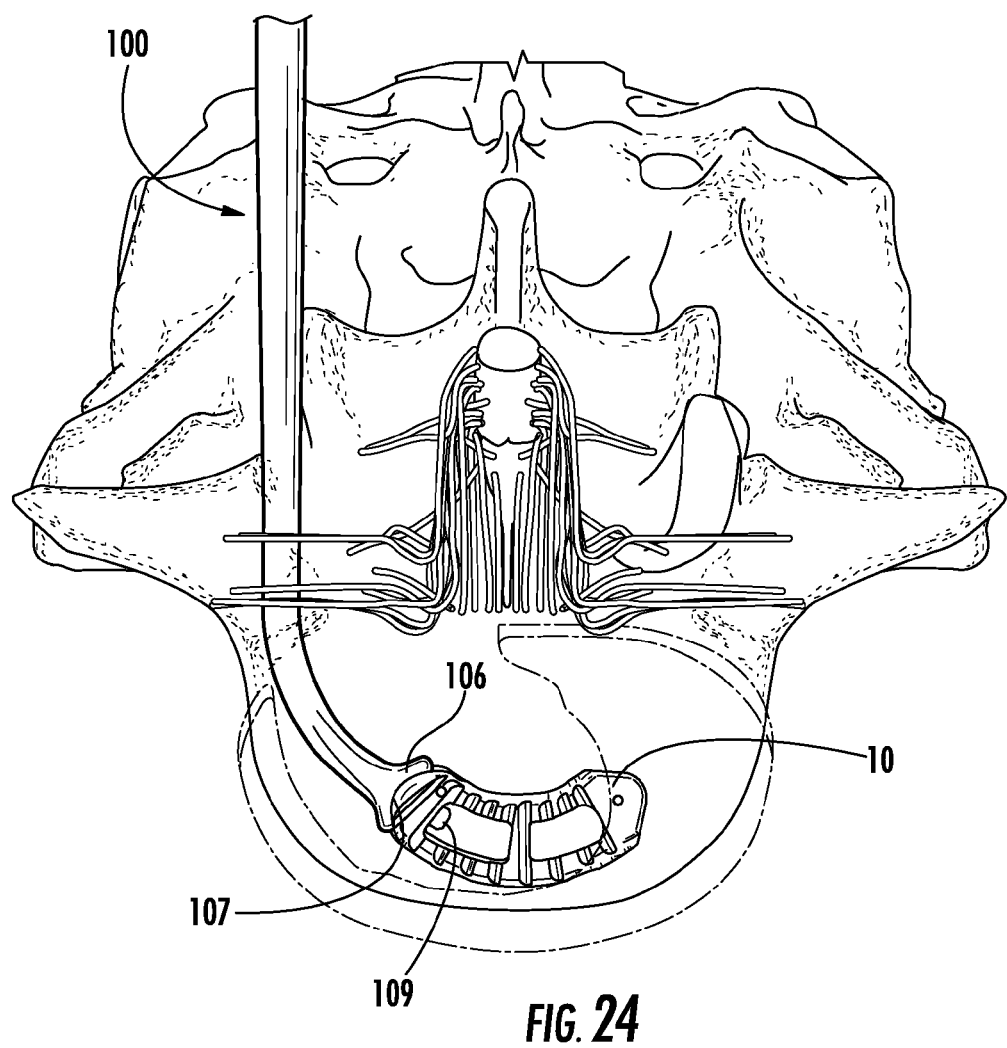
FIG. 24 is a perspective view of a cross section of a portion of a human spine, showing the tamp of FIG. 23 engaged with an implant.

FIG. 23 illustrates a tamp leveler 100 that includes a handle 101 and a shaft 102 that extends from the handle 101 at any suitable angle. As illustrated, shaft 102 may include one or more bends if desired to accommodate the patient's anatomy and provide a more unobstructed view into the disc space. In some embodiments, a neck 104 connects an engagement head 106 to the shaft 104. If used, neck 104 may extend from shaft 104 at any suitable angle and may include any suitable radius of curvature to accommodate the patient's anatomy and the disc space. Engagement head 106 includes a surface 107 that is shaped and configured to be received within channel 12 of implant 10. Protrusion 109 extends from surface 107 and is configured to be received within aperture 26 of channel 12. Protrusion 109 may have any suitable cross section and may have any suitable length. FIG. 24 illustrates tamp leveler 100 engaged with implant 10 and positioned within the disc space.

Figure 25:
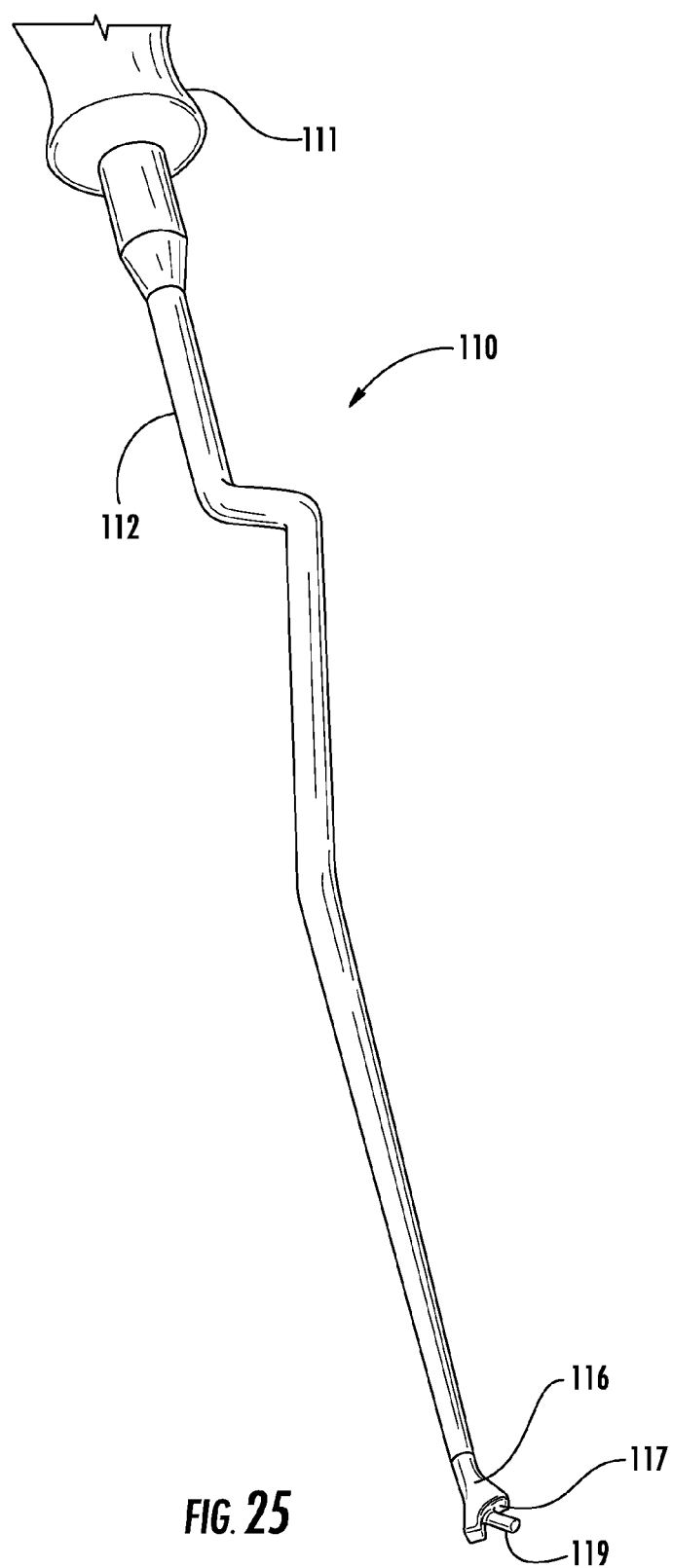
FIG. 25 is a perspective view of another tamp of an embodiment of this invention.

FIG. 25 illustrates a tamp leveler 110 that includes a handle 111 and a shaft 112 that extends from the handle 111 at any suitable angle. As illustrated, shaft 112 may include one or more bends if desired to accommodate the patient's anatomy and provide a more unobstructed view into the disc space. Engagement head 116 extends from the shaft 112. If desired, a neck having any suitable angle and radius of curvature may connect engagement head 116 with shaft 114. Engagement head 116 includes a surface 117 that is shaped and configured to be received within channel 12 of implant 10. Protrusion 119 extends from surface 117 and is configured to be received within aperture 26 of channel 12. Protrusion 119 may have any suitable cross section and may have any suitable length.

Figure 26:
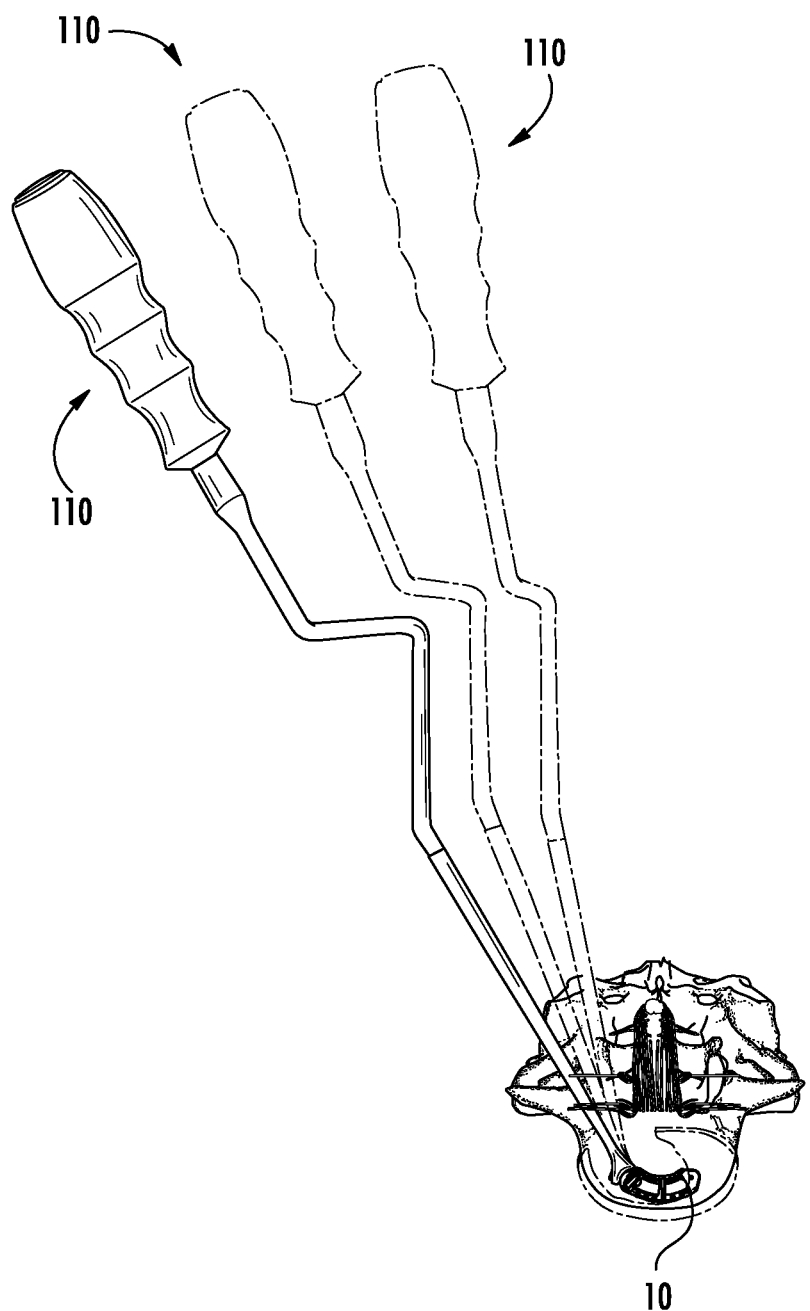
FIG. 26 illustrates various angle handles of the tamp of FIG. 25, shown in use with an implant and a portion of the human spine.

FIG. 26 illustrates various tamp levelers 110 engaged with implant 10 and positioned within the disc space. As shown in FIG. 26, shaft 112 may include various bends having any suitable angle. When the implant is properly aligned within the disc space, at least a portion of the shaft 112 is approximately perpendicular to the spine.

Figure 27:
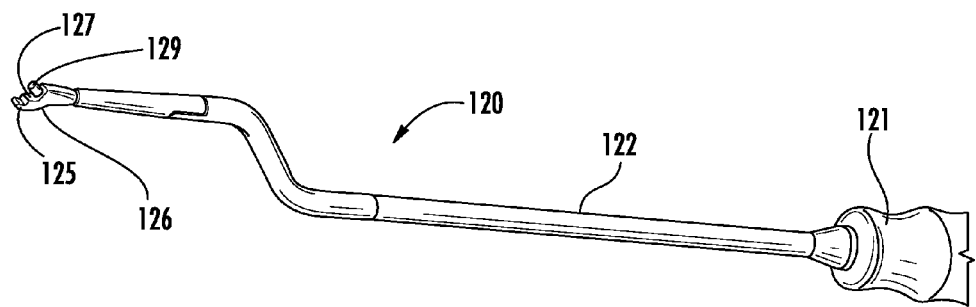
FIG. 27 is a perspective view of another tamp of an embodiment of this invention.
Figure 28:
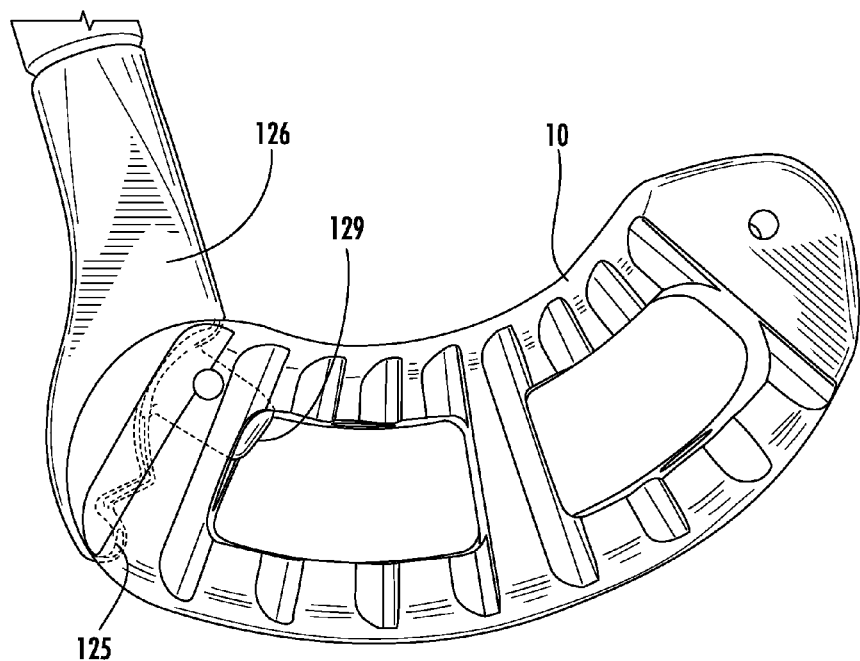
FIG. 28 is a perspective view of the tamp of FIG. 27 engaged with an implant.

FIG. 27 illustrate a tamp leveler 120 according to an embodiment of the invention. Tamp leveler 120 includes a handle 121 and a shaft 122 that extends from the handle 121 at any suitable angle. As shown, shaft 122 may include one or more bends if desired to accommodate the patient's anatomy and provide a more unobstructed view into the disc space. Engagement head 126 extends from the shaft 122. If desired, a neck having any suitable angle and radius of curvature may connect engagement head 126 with shaft 122. Engagement head 126 includes a surface 127 that is shaped and configured to be received within channel 12 of implant 10. Protrusion 129 extends from surface 127 and is configured to be received within aperture 26 of channel 12. Protrusion 129 may have any suitable cross section and may have any suitable length. In some embodiments, the engagement head 126 includes a notch 125 that is shaped and configured to rest in the channel 12 to help keep tamp leveler 120 balanced, as shown in FIG. 28. In particular, notch 125 helps maintain tamp leveler 120 within the channel 12 if the surgeon pulls the leveler away from the implant. Protrusion 129 helps prevent the surgeon or other personnel from pushing the shaft 122 too far midline.

Figure 29:
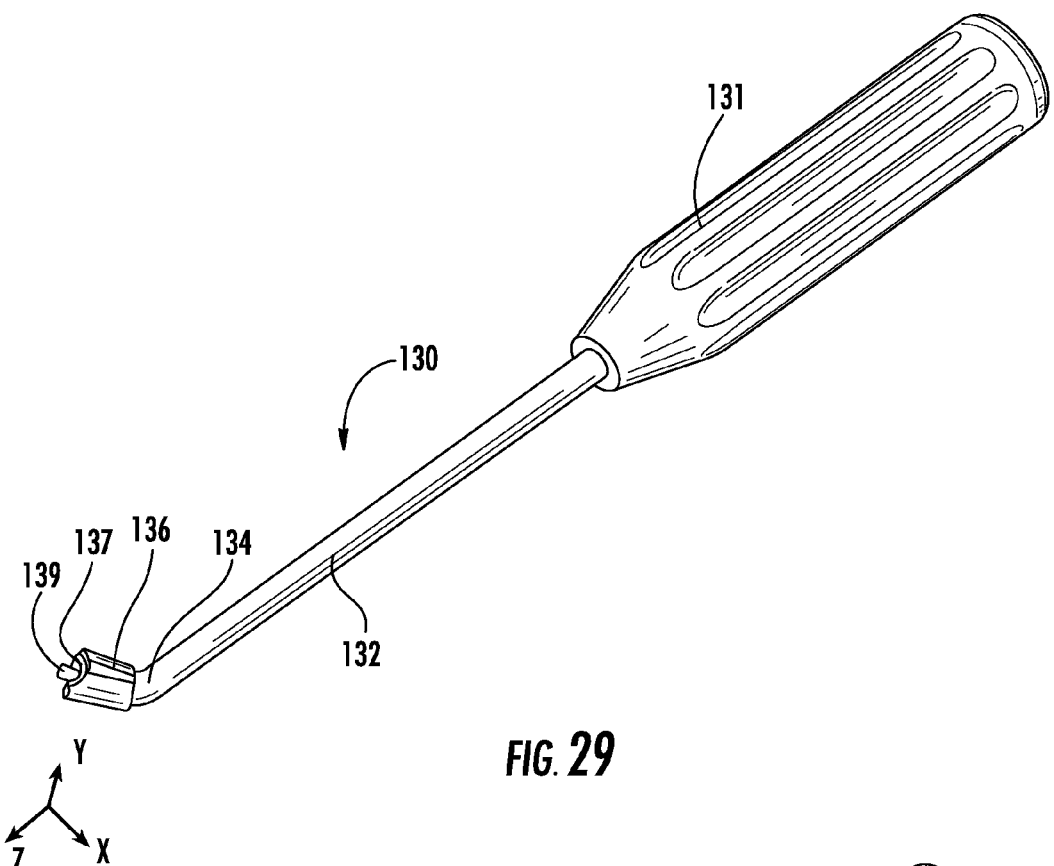
FIG. 29 is a perspective view of another tamp of an embodiment of this invention.
Figure 30:
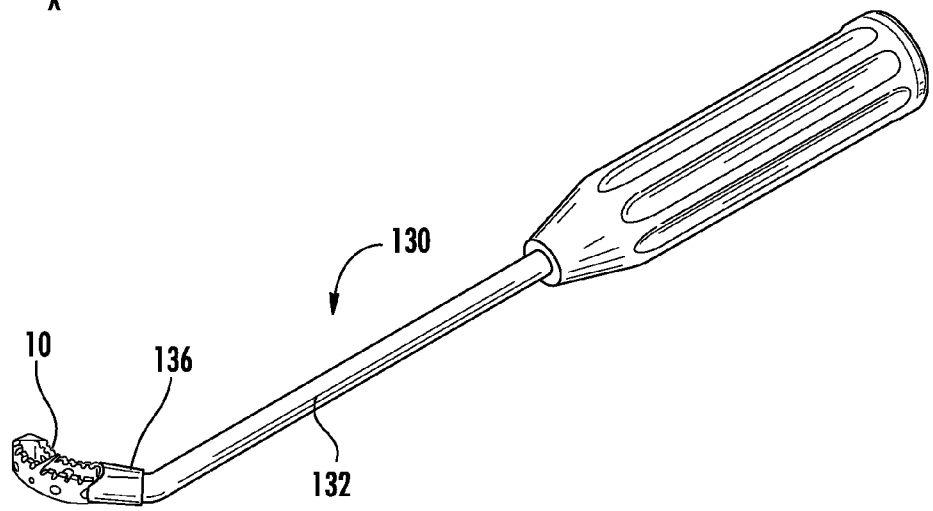
FIG. 30 is a perspective view of the tamp of FIG. 29 engaged with an implant.
Figure 31:
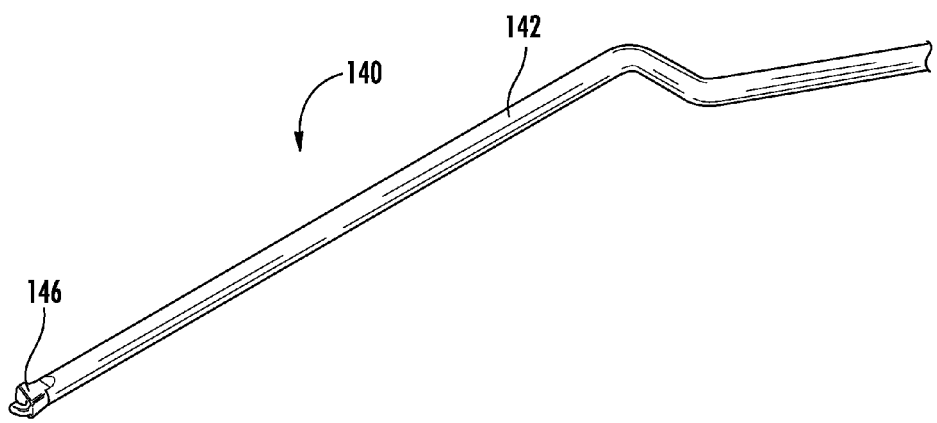
FIG. 31 is a perspective view of another tamp of an embodiment of this invention.

FIG. 29 illustrates a tamp leveler 130 that includes a handle 131 and a shaft 132 that extends from the handle 131. Although shaft 132 is illustrated as straight, shaft 132 may include one or more bends if desired. Neck 134 having any suitable angle and radius of curvature connects engagement head 136 with shaft 134, although in other embodiments neck 134 is not used. Engagement head 136 includes a surface 137 that is shaped and configured to be received within channel 12 of implant 10. Protrusion 139 extends from surface 137 and is configured to be received within aperture 26 of channel 12. Protrusion 137 may have any suitable cross section and may have any suitable length. FIG. 30 illustrates tamp leveler 130 engaged with implant 10.

Figure 32:
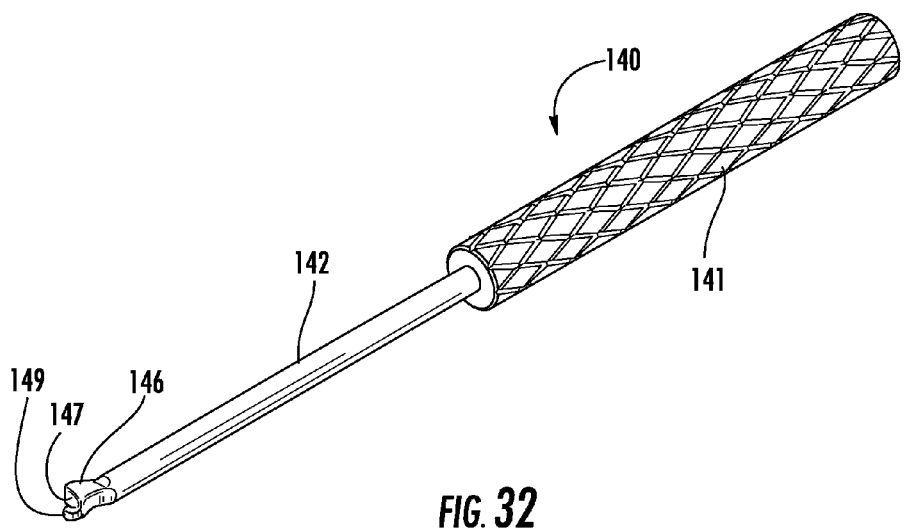
FIG. 32 is a perspective view of another tamp of an embodiment of this invention.
Figure 33:
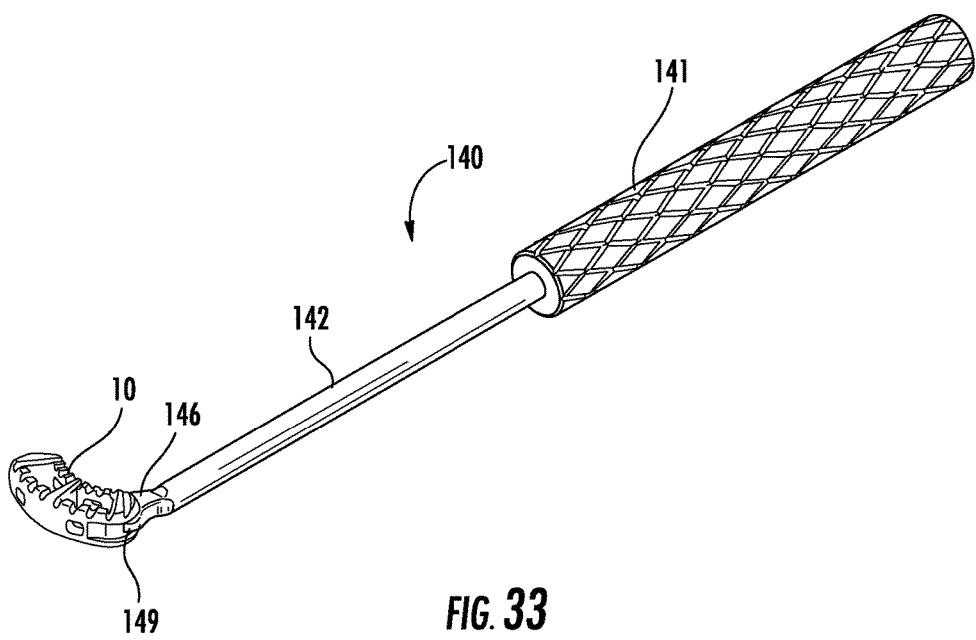
FIG. 33 is a perspective view of the tamp of FIG. 32 engaged with an implant.

FIGS. 30-33 illustrate a tamp leveler 140 that includes a handle 141 and a shaft 142 that extends from the handle 141. Shaft 142 may extend from handle 141 at any suitable angle and may include one or more bends (FIG. 31) or may be straight (FIG. 32). As shown, engagement head 146 extends from shaft 142, although a neck having any suitable angle and radius of curvature may be used to connect engagement head 146 with shaft 144 if desired. Engagement head 146 includes a surface 147 that is shaped and configured to be received within channel 12 of implant 10. Hook 149 extends from an end of surface 147 and is configured to be received within aperture 26 of channel 12. Hook 149 may have any suitable cross section, may have any suitable length, and may extend from surface 149 at any desired location or angle. FIG. 33 illustrates tamp leveler 140 engaged with implant 10.

As described, endless variations to the tamp levelers described herein are envisioned depending on the implant with which the tamp leveler is to be used, the patient's anatomy, the surgical approach, etc. In some embodiments, the features described above are configured so that, when the tamp leveler is engaged with the implant and when the implant reaches proper alignment within the disc space, at least a portion of the shaft of the tamp leveler is oriented approximately perpendicular to the spine to indicate to the surgeon or other user that the implant has the correct rotation. When the relevant portion of the tamp leveler is determined to be perpendicular, the surgeon or other personnel has a level of confidence that the implant is in a proper position in the disc space so that he can stop manipulating the implant and move onto secondary portions of the operation. This saves time from bringing in additional x-ray equipment and exposing the operating room to more radiation. This also allows the surgeon to continue with pedicle screws and to take a final x-ray when the procedure is complete to confirm placement and alignment if so desired.

When the implant is properly aligned, the teeth of the implant should be in the caudal-cephaled position, with the convex anterior wall resting up against the anterior annulus in the anterior third of the disc space. Bone graft material may then be place around or behind the implant, depending on positioning of the implant. The tantalum markers are visible on x-ray to aid in the confirmation of proper final position.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

The invention claimed is:

1. A spinal implant comprising a body comprising:
   a front surface, a rear surface, a top surface, and a bottom surface;
   a first end comprising an arcuate surface and a channel having a channel surface that is recessed relative to the arcuate surface; and
   at least one alignment guide comprising:
      a first marking having a first edge and a second edge distal from the first edge and extending along a non-edge portion of the arcuate surface, wherein a shade of the first marking is visually distinct from a shade of the channel surface and a shade of the arcuate surface, and wherein the first marking comprises a width between the first edge and the second edge of the first marking that extends along the arcuate surface; and
      a second marking having a first edge and a second edge distal from the first edge and extending along a non-edge portion of the channel surface, wherein a shade of the second marking is visually distinct from the shade of the channel surface and the shade of the arcuate surface, and wherein the second marking comprises a width between the first edge and the second edge of the second marking that extends along the channel surface,
   wherein the spinal implant is insertable along an insertion axis and movable between a first configuration in which the spinal implant is not properly aligned within a disc space and a second configuration in which the spinal implant is properly aligned within the disc space,
   wherein the first and second markings are positioned on the spinal implant such that:
      (1) when in the first configuration and viewed along the insertion axis, the spinal implant provides a visual indication that the spinal implant is not properly aligned within the disc space; and
      (2) when in the second configuration and viewed along the insertion axis, the spinal implant provides a visual indication that the spinal implant is properly aligned within the disc space,
   wherein, when the spinal implant is in the first configuration and viewed along the insertion axis, the first edge of the first marking is offset from the first edge of the second marking and the second edge of the first marking is offset from the second edge of the second marking to provide the visual indication that the spinal implant is not properly aligned within the disc space, and
   wherein, when the spinal implant is in the second configuration and viewed along the insertion axis, the first edge of the first marking is aligned with the first edge of the second marking and the second edge of the first marking is aligned with the second edge of the second marking to provide the visual indication that the spinal implant is properly aligned within the disc space.

2. The spinal implant of claim 1, wherein the implant is generally kidney-shaped.

3. The spinal implant of claim 1, wherein the alignment guide further comprises a third marking extending in a vertical direction along the arcuate surface.

4. The spinal implant of claim 3, wherein the first, second, and third markings are configured such that they appear to align along a single axis when the implant is in the second configuration and such that they do not appear to align along the single axis when the implant is in the first configuration.

5. The spinal implant of claim 1, further comprising an aperture within the channel.

6. A kit comprising:
   the spinal implant of claim 5; and
   a tamp leveler comprising:
      a shaft and an engagement head extending from the shaft; shaft,
      wherein the engagement head comprises a protrusion or hook for engaging with the aperture of the implant.

7. The kit of claim 6, wherein a surface of the engagement head is configured to be received within the channel of the implant.

8. The kit of claim 6, wherein the engagement head further comprises a ledge configured to be received within the channel of the implant.

9. The kit of claim 6, wherein the engagement head further comprises a notch that extends from an end of the engagement head and that is configured to rest within the channel of the implant.

10. The spinal implant of claim 1, further comprising at least one window along either the rear surface or the front surface.

11. A kit comprising:
    the spinal implant of claim 10; and
    a tamp leveler comprising:
       a shaft and an engagement head extending from the shaft,
       wherein the engagement head comprises a feature for cooperating with the at least one window.

12. The kit of claim 11, wherein the feature is configured to rest within the at least one window.

13. The kit of claim 11, wherein the feature is configured as a hook that hooks into the at least one window.

14. The kit of claim 11, wherein the feature is a protrusion that hooks into the at least one window.

15. The kit of claim 11, wherein the engagement head further comprises a ledge configured to be received within the channel of the implant.

16. The kit of claim 15, wherein the feature is a protrusion that extends from the engagement head.

17. The spinal implant of claim 1, wherein the shade of the first marking and the shade of the second marking are the same.

18. The spinal implant of claim 1, wherein, in the first configuration and when viewed along the insertion axis, one of the first edge or the second edge of the first marking is between the first edge and the second edge of the second marking.

19. A method of implanting a spinal implant within a disc space, the method comprising:
    inserting the spinal implant along an insertion axis into the disc space, wherein the spinal implant comprises a body comprising:
       a front surface, a rear surface, a top surface, and a bottom surface;
       a first end comprising an arcuate surface and a channel having a channel surface that is recessed relative to the arcuate surface; and
       at least one alignment guide comprising:
          a first marking having a first edge and a second edge distal from the first edge and extending along a non-edge portion of the arcuate surface, wherein a shade of the first marking is visually distinct from a shade of the channel surface and a shade of the arcuate surface, and wherein the first marking comprises a width between the first edge and the second edge of the first marking that extends along the arcuate surface; and a second marking having a first edge and a second edge distal from the first edge and extending along a non-edge portion of the channel surface, wherein a shade of the second marking is visually distinct from the shade of the channel surface and the shade of the arcuate surface, and wherein the second marking comprises a width between the first edge and the second edge of the second marking that extends along channel surface;

viewing the spinal implant along the insertion axis and determining whether the spinal implant is in a first configuration in which the spinal implant is not properly aligned within a disc space or in a second configuration in which the spinal implant is properly aligned within the disc space, wherein, when the spinal implant is in the first configuration and viewed along the insertion axis, the first edge of the first marking is offset from the first edge of the second marking and the second edge of the first marking is offset from the second edge of the second marking to provide a visual indication that the spinal implant is not properly aligned within the disc space, and wherein, when the spinal implant is in the second configuration and viewed along the insertion axis, the first edge of the first marking is aligned with the first edge of the second marking and the second edge of the first marking is aligned with the second edge of the second marking to provide a visual indication that the spinal implant is properly aligned within the disc space; and if the spinal implant is in the first configuration, moving the spinal implant until the spinal implant is in the second configuration and properly aligned within the disc space.

* * * * *